(12) United States Patent
Druma

(10) Patent No.: US 9,192,420 B2
(45) Date of Patent: Nov. 24, 2015

(54) SURGICAL SYSTEM AND METHODS OF USE

(71) Applicant: KYPHON SARL, Neuchatel (CN)

(72) Inventor: Calin Druma, San Jose, CA (US)

(73) Assignee: KYPHON SARL, Neuchatel (CH)

( * ) Notice: Subject to any disclaimer, the term of this patent is extended or adjusted under 35 U.S.C. 154(b) by 184 days.

(21) Appl. No.: 13/749,430

(22) Filed: Jan. 24, 2013

(65) Prior Publication Data

US 2014/0207193 A1   Jul. 24, 2014

(51) Int. Cl.
A61B 17/58 (2006.01)
A61B 17/60 (2006.01)
A61F 2/00 (2006.01)
A61B 17/88 (2006.01)

(52) U.S. Cl.
CPC .................. A61B 17/8855 (2013.01)

(58) Field of Classification Search
CPC ............. A61F 2/44; A61F 2/441; A61F 2/00; A61B 17/58; A61B 17/60; A61B 17/885; A61B 17/8852; A61B 17/8855; A61B 17/8858; A61M 25/00; A61M 25/10; A61M 25/0119; A61M 25/1002; A61M 2025/1065
USPC ........... 623/17.11–17.16; 606/27, 105, 279, 9
See application file for complete search history.

(56) References Cited

U.S. PATENT DOCUMENTS

| 4,338,942 | A | * | 7/1982 | Fogarty | 606/194 |
| 4,526,175 | A | * | 7/1985 | Chin et al. | 606/192 |
| 4,969,888 | A | | 11/1990 | Scholten et al. | |
| 5,549,679 | A | * | 8/1996 | Kuslich | 623/17.12 |
| 5,919,163 | A | | 7/1999 | Glickman | |
| 5,972,015 | A | * | 10/1999 | Scribner et al. | 606/192 |
| 6,063,112 | A | * | 5/2000 | Sgro | 623/1.12 |
| 6,235,043 | B1 | | 5/2001 | Reiley et al. | |
| 6,248,110 | B1 | * | 6/2001 | Reiley et al. | 606/93 |
| 6,440,138 | B1 | * | 8/2002 | Reiley et al. | 606/79 |
| 6,616,678 | B2 | * | 9/2003 | Nishtala et al. | 606/198 |
| 6,979,341 | B2 | * | 12/2005 | Scribner et al. | 606/192 |
| 7,261,720 | B2 | * | 8/2007 | Stevens et al. | 606/105 |
| 7,722,624 | B2 | * | 5/2010 | Boucher et al. | 606/105 |
| 7,837,733 | B2 | * | 11/2010 | Collins et al. | 623/17.12 |
| 8,221,460 | B2 | | 7/2012 | Mathews | |
| 8,409,212 | B2 | * | 4/2013 | Lu et al. | 606/94 |
| 8,734,458 | B2 | * | 5/2014 | O'Halloran et al. | 606/92 |
| 8,734,459 | B1 | * | 5/2014 | Alobaid | 606/92 |
| 8,900,304 | B1 | * | 12/2014 | Alobaid | 623/17.12 |
| 2002/0068974 | A1 | * | 6/2002 | Kuslich et al. | 623/17.11 |
| 2002/0095114 | A1 | | 7/2002 | Palasis | |
| 2002/0147497 | A1 | * | 10/2002 | Belef et al. | 623/17.12 |
| 2003/0028251 | A1 | * | 2/2003 | Mathews | 623/17.16 |
| 2003/0088249 | A1 | * | 5/2003 | Furderer | 606/61 |

(Continued)

FOREIGN PATENT DOCUMENTS

WO    2006034396 A2    3/2006

*Primary Examiner* — Eduardo C Robert
*Assistant Examiner* — Michelle C. Eckman
(74) *Attorney, Agent, or Firm* — Sorell Lenna & Schmidt LLP

(57) ABSTRACT

A surgical system including an expandable device is provided, including an inflatable body and a compliant sleeve. The compliant sleeve includes a distal end, a proximal end, and a cavity extending from the proximal end to the oppositely disposed distal end configured to receive a portion of the inflatable body. The cavity is defined by an inner wall and an outer wall of the compliant sleeve. The distal end of the compliant sleeve forms a closed portion of the cavity and the proximal end includes an opening.

20 Claims, 7 Drawing Sheets

(56) References Cited

U.S. PATENT DOCUMENTS

| | | | |
|---|---|---|---|
| 2004/0186471 A1* | 9/2004 | Trieu | 606/61 |
| 2004/0215344 A1* | 10/2004 | Hochschuler et al. | 623/17.12 |
| 2005/0015148 A1* | 1/2005 | Jansen et al. | 623/17.11 |
| 2005/0090901 A1* | 4/2005 | Studer | 623/17.12 |
| 2005/0131267 A1* | 6/2005 | Talmadge | 600/3 |
| 2005/0234498 A1* | 10/2005 | Gronemeyer et al. | 606/192 |
| 2005/0245938 A1* | 11/2005 | Kochan | 606/92 |
| 2005/0288678 A1* | 12/2005 | Reiley et al. | 606/93 |
| 2006/0212022 A1 | 9/2006 | Gellman | |
| 2006/0265076 A1* | 11/2006 | Carter et al. | 623/17.16 |
| 2006/0271061 A1* | 11/2006 | Beyar et al. | 606/105 |
| 2007/0055276 A1* | 3/2007 | Edidin | 606/92 |
| 2007/0073402 A1* | 3/2007 | Vresilovic et al. | 623/17.12 |
| 2007/0088436 A1* | 4/2007 | Parsons et al. | 623/17.11 |
| 2007/0135921 A1* | 6/2007 | Park | 623/17.12 |
| 2007/0150061 A1* | 6/2007 | Trieu | 623/17.12 |
| 2007/0156242 A1* | 7/2007 | Lin et al. | 623/17.12 |
| 2007/0162136 A1* | 7/2007 | O'Neil et al. | 623/17.12 |
| 2007/0173935 A1* | 7/2007 | O'Neil et al. | 623/17.11 |
| 2007/0225705 A1* | 9/2007 | Osorio et al. | 606/60 |
| 2007/0225809 A1* | 9/2007 | Ray | 623/17.12 |
| 2007/0233258 A1* | 10/2007 | Hestad et al. | 623/17.12 |
| 2007/0255285 A1* | 11/2007 | Trieu | 606/86 |
| 2007/0255406 A1* | 11/2007 | Trieu | 623/17.11 |
| 2007/0270950 A1* | 11/2007 | Trieu | 623/17.11 |
| 2008/0027554 A1* | 1/2008 | Talmadge | 623/17.16 |
| 2008/0125782 A1* | 5/2008 | Rydell et al. | 606/79 |
| 2008/0195207 A1* | 8/2008 | Lin et al. | 623/17.12 |
| 2008/0215151 A1* | 9/2008 | Kohm et al. | 623/17.11 |
| 2008/0243249 A1* | 10/2008 | Kohm et al. | 623/17.12 |
| 2008/0249604 A1* | 10/2008 | Donovan et al. | 623/1.15 |
| 2009/0088788 A1 | 4/2009 | Mouw | |
| 2009/0112221 A1* | 4/2009 | Burke et al. | 606/102 |
| 2009/0222093 A1* | 9/2009 | Liu et al. | 623/17.12 |
| 2009/0234457 A1* | 9/2009 | Lotz et al. | 623/17.16 |
| 2009/0299401 A1* | 12/2009 | Tilson | 606/192 |
| 2009/0299476 A1* | 12/2009 | Diwan et al. | 623/17.12 |
| 2010/0137923 A1* | 6/2010 | Greenhalgh et al. | 606/86 R |
| 2010/0262240 A1* | 10/2010 | Chavatte et al. | 623/17.11 |
| 2011/0153021 A1* | 6/2011 | Diwan | 623/17.16 |
| 2011/0196499 A1* | 8/2011 | Boucher et al. | 623/17.16 |
| 2011/0295370 A1* | 12/2011 | Suh et al. | 623/17.12 |
| 2012/0010713 A1* | 1/2012 | O'Halloran et al. | 623/17.12 |
| 2012/0130161 A1 | 5/2012 | Lauryssen et al. | |
| 2012/0165941 A1* | 6/2012 | Rabiner et al. | 623/17.12 |
| 2012/0277811 A1 | 11/2012 | Lauchner et al. | |
| 2013/0204268 A1* | 8/2013 | Mafi et al. | 606/105 |
| 2014/0257417 A1* | 9/2014 | Diwan et al. | 606/86 A |
| 2014/0277465 A1* | 9/2014 | Teisen et al. | 623/17.12 |

* cited by examiner

SURGICAL SYSTEM AND METHODS OF USE

TECHNICAL FIELD

The present disclosure relates generally to instruments and devices for spinal surgery, and more particularly to expandable devices including a compliant sleeve configured to prevent rupture of an inflatable body in situ. Methods of using such devices are also provided.

BACKGROUND

Height loss is commonly associated with spinal fractures, typically referred to as vertebral compression fractures. A large segment of osteoporotic patients experience vertebral compression fractures, with an estimated 700,000 such fractures occurring annually. Kyphoplasty is a minimally invasive procedure that is used to treat vertebral compression fractures using a combination of vertebroplasty utilizing bone cement with balloon catheter technology. The kyphoplasty procedure restores height of the collapsed spinal bone, which diminishes associated back pain.

In a kyphoplasty procedure, an inflatable balloon tamp (IBT) is inserted inside a fractured vertebral body. The IBT is inflated to create a cavity that is filled with bone cement to restore height of the vertebral body.

Using conventional kyphoplasty procedures, the bone cement cannot be injected into the vertebral body cavity next to an inflated IBT at high pressure without risking a loss of pressure due to the adjacent IBT rupturing. This restricts the amount of height restoration that can be achieved from the procedure. This disclosure describes an improvement over these prior art technologies.

SUMMARY

In one embodiment, in accordance with the principles of the present disclosure an expandable device is provided including an inflatable device and a compliant sleeve having a longitudinal axis. The compliant sleeve includes a distal end, a proximal end, and a cavity extending from the proximal end to the oppositely disposed distal end along the longitudinal axis. The cavity is defined by an inner wall and an outer wall of the compliment sleeve. The distal end of the compliant sleeve forms a closed portion of the cavity and the proximal end has an opening. The cavity is configured to receive a portion of the inflatable body.

BRIEF DESCRIPTION OF THE DRAWINGS

The present disclosure will become more readily apparent from the specific description accompanied by the following drawings, in which:

FIG. 1b is a side, cross-sectional view of the expandable device shown in FIG. 1a;

FIG. 1c is a side view of a component of the expandable device shown in FIG. 1a;

FIG. 1d is a cross-sectional view of an proximal end of a component of the expandable device shown in FIG. 1a;

FIG. 2 is a side, cross-sectional view of a sleeve part in accordance with the principles of the present disclosure disposed within a component of the expandable device shown in FIG. 1a;

Like reference numerals indicate similar parts throughout the figures.

DETAILED DESCRIPTION

Figure 1A:
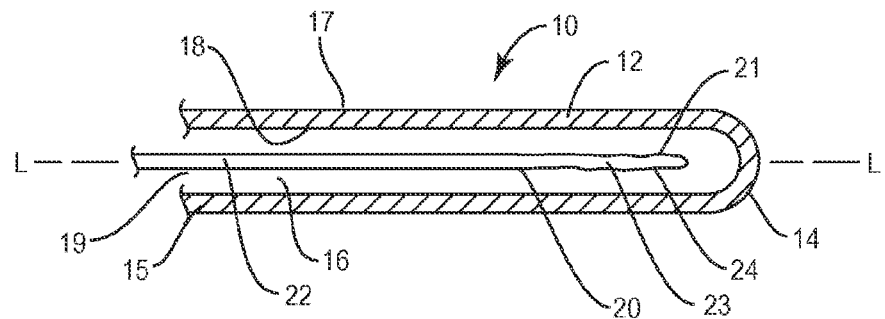
FIG. 1a is a side, cross-sectional view of an expandable device in accordance with the principles of the present disclosure.
Figure 1B:
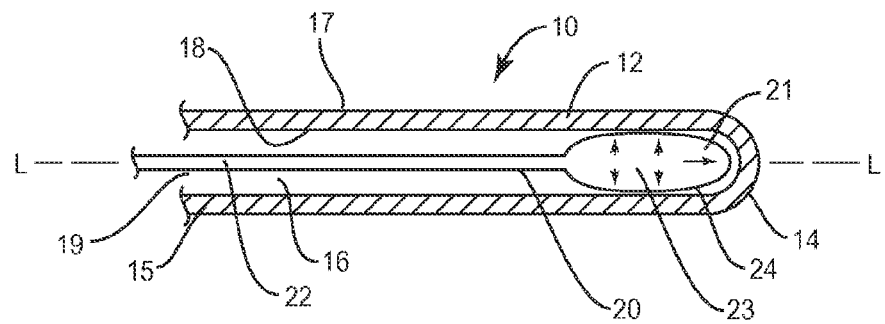
Figure 1C:
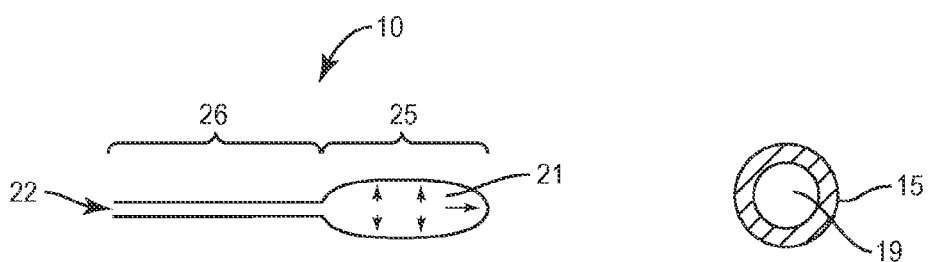
Figure 1D:
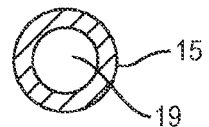

The exemplary embodiments of surgical system are discussed in terms of medical devices for the treatment of musculoskeletal disorders and more particularly in terms of a system comprising an expandable device including an inflatable body and a compliant sleeve configured to protect and prevent damage to the inflatable body when bone void filler is placed adjacent to the inflatable body and a method for treating a spine.

In one embodiment, the system includes a protective sleeve made of silicone. It is envisioned that the protective sleeve may also be made from thermoplastic polyurethane (TPU), polyethylene terephthalate (PET), polyimide (nylon) or chronoprene. The protective sleeve houses an inflatable device, such as for example, an inflatable balloon tamp configured for use in a balloon kyphoplasty procedure. The protective sleeve prevents bone material, such as for example bone cement from contacting the inflatable balloon tamp when the protective is inserted into or adjacent a vertebral body and bone cement is delivered to the vertebral body to treat a disorder, such as, for example, a fracture and/or restore the height of the vertebral body. It is envisioned that the protective sleeve will prevent bone cement from contacting the inflatable balloon tamp when the bone cement is delivered to a side of the vertebral body that is contralateral to a side of the vertebral body in which the protective sleeve is inserted.

In one embodiment, a first inflatable balloon tamp is inserted into a first side of a vertebral body. The first inflatable balloon tamp is then inflated such that cancellous bone of the vertebral body is pushed toward the cortical walls of the vertebral body to form a cavity. A protective sleeve is then inserted into an opposite second side of the vertebral body. It is envisioned that the protective sleeve can be inserted into the vertebral body using an instrument, such as, for example, a stylus. It is further envisioned that the protective sleeve may be inserted into the vertebral body through a hole drilled into the vertebral body. The stylus is removed and a second inflatable bone tamp is inserted into the protective sleeve and inflated within the protective sleeve. Once the second inflatable balloon tamp is inflated, the first inflatable balloon tamp is removed from the vertebral body. Bone cement is delivered to the cavity formed by the first inflatable balloon tamp. The bone cement remains in the cavity until it cures. Once the bone cement cures, the second inflatable balloon tamp is deflated and removed from the protective sleeve. The protective sleeve is then removed from the vertebral body. It is envisioned that bone cement may be delivered to the vertebral body after the protective sleeve has been removed from the vertebral body to fill the cavity formed by the first inflatable balloon tamp, a cavity formed by inflation of the second inflatable balloon tamp or another void in the vertebral body, depending upon the requirement of a particular application.

It is envisioned that the system of the present disclosure may be employed to treat spinal disorders such as, for example, degenerative disc disease, vertebral compression fractures, osteoporosis, spondylolisthesis, stenosis, scoliosis and other curvature abnormalities, kyphosis, tumor and fractures. It is contemplated that the system of the present disclosure may be employed with other osteal and bone related applications, including those associated with diagnostics and therapeutics. It is further contemplated that the disclosed system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The system of the present disclosure may also be alternatively employed with procedures for treating the lumbar, cervical, thoracic, sacral and pelvic regions of a spinal column. The system of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, distal and proximal, are for illustrative purposes only and can be varied within the scope of the disclosure. For example, the references "upper" and "lower" are relative and used only in the context to the other, and are not necessarily "superior" and "inferior".

Further, as used in the specification, including the appended claims, "treating" or "treatment" of a disease or condition refers to performing a procedure that may include administering one or more materials to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament and/or bone, repairing a fracture or break in bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following disclosure includes a description of a surgical system, including a protective sleeve configured for disposal of an inflatable bone tamp (IBT), related components and methods of employing the surgical system in accordance with the principles of the present disclosure. Alternate embodiments are also disclosed. References will now be made in detail to the exemplary embodiments of the present disclosure, which are illustrated in the accompanying figures. Turning now to FIGS. 1a-6, there are illustrated components of a surgical system in accordance with the principles of the present disclosure.

The components of the disclosed system can be fabricated from biologically acceptable materials suitable for medical applications, including metals, synthetic polymers, ceramics and bone material and/or their composites, depending on the particular application and/or preference of a medical practitioner. For example, the components of the disclosed system, individually or collectively, can be fabricated from materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the disclosed system may have material composites, including the above materials, to achieve various desired characteristics such as strength, rigidity, elasticity, compliance, biomechanical performance, durability and radiolucency or imaging preference. The components of the disclosed system, individually or collectively, may also be fabricated from a heterogeneous material such as a combination of two or more of the above-described materials. The components of the disclosed system may be monolithically formed, integrally connected or include fastening elements and/or instruments, as described herein.

The disclosed system includes an expandable device 10 including a compliant sleeve 12 defining a longitudinal axis L. Sleeve 12 includes a distal end 14, a proximal end 15, and a U-shaped cavity 16 extending from end 15 to end 14 along axis L. Cavity 16 is defined by an outer wall 17 and an inner wall 18 of sleeve 12. End 14 forms a closed portion of cavity 16 and end 15 forms an open portion of cavity 16. An opening 19 at the open portion of cavity 16. Cavity 16 is configured to receive an inflatable balloon tamp such as, for example an inflatable body 20.

Body 20 includes a distal end 21 at a distal end portion 25 and a proximal end portion 26 configured to engage a fill tube used to inflate portion 25. Portion 26 includes a lumen 22 extending to portion 25. Lumen 22 continuous with a fillable cavity 23 located in portion 25. Cavity 23 is defined by a wall 24 configured to inflate upon receiving a material, such as, for example, a gas or fluid. Cavity 23 is in communication with lumen 22 and a fill tube so that material delivered from the fill tube inflates cavity 23 outwardly toward wall 18. It is envisioned that the material used to inflate cavity 23 can be in the form of a liquid or a gas, for example, either saline or compressed air. When inflated, wall 24 expands from a deflated configuration illustrated in FIG. 1a to an inflated configuration illustrated in FIG. 1b. When wall 24 is in the inflated configuration wall 24 pushes outwardly against wall 18.

Body 20 is configured to be inserted through opening 19 such that portion 25 is disposed within cavity 16. In one embodiment, cavity 16 has a length sufficient for disposal of portion 26 when portion 25 is disposed within cavity 16. Body 20 is inserted into sleeve 12 with wall 24 in the deflated configuration either before sleeve 12 is delivered to a surgical site, such as, for example, a vertebral body or after sleeve 12 is delivered to the surgical site.

Sleeve 12 has thickness defined by the distance between wall 18 and wall 17 configured to prevent wall 24 from moving from the inflated configuration to the deflated configuration upon delivery of a material, such as, for example, a bone void filler adjacent to a surgical site. In one embodiment, the thickness of sleeve 12 is within a range from about 0.001 inches to about 0.010 inches. It is envisioned that sleeve 12 may include any thickness, depending upon the requirements of a particular application. It is further envisioned that the thickness of sleeve 12 will permit expansion as wall 24 moves from the deflated configuration to the inflated configuration. It is contemplated that sleeve 12 can be fabricated from biologically acceptable materials suitable for medical apparatuses including silicone, chloroprene, thermoplastic polyurethane (TPU), polyethylene terephthalate (PET), polyamide (Nylon) or any suitable combination thereof.

Figure 2:
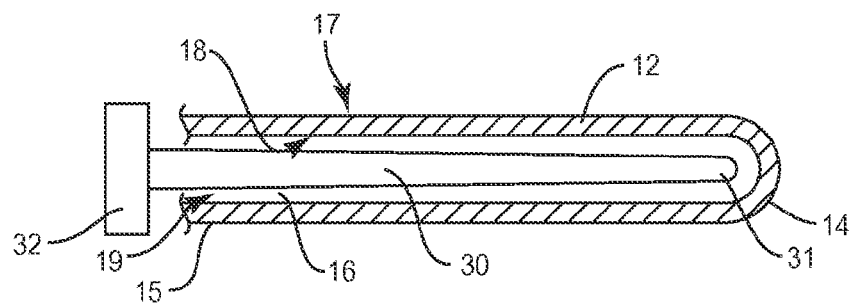

In one embodiment, sleeve 12 is inserted into an access hole in a bone, such as a vertebral body, using a sleeve-port 30, as shown in FIG. 2. Sleeve-port 30 includes a distal end 31 and a proximal end 32 and is configured to enter cavity 16 through opening 19. Sleeve-port 30 extends continuously from end 15 to end 14 along axis L. In one embodiment sleeve-port 31 is tapered at end 31 for ease of retraction from sleeve 12. In one embodiment, end 32 is configured as a handle that is positioned on end 15. Sleeve-port 30 is configured to be removed from sleeve 12 once sleeve 12 is inserted into or adjacent in surgical site.

Figure 3:
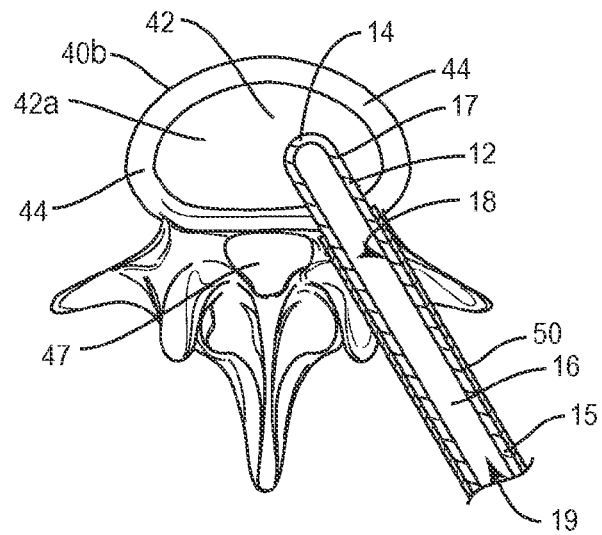
FIG. 3 is a plan view, in part cross-section, of a component of the expandable device shown in FIG. 1a disposed with a vertebra.
Figure 3A:
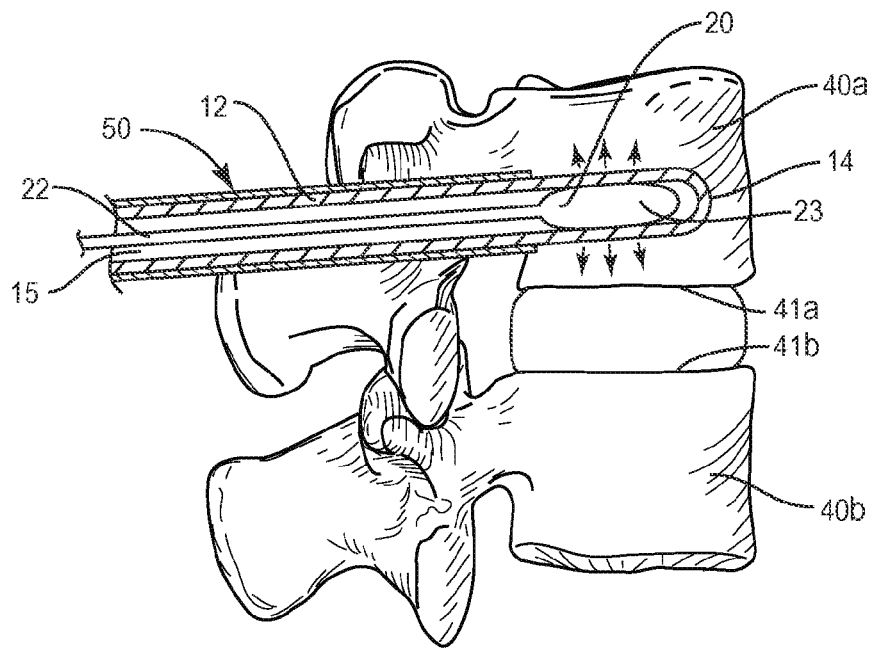
FIG. 3a is a side, cross-sectional view of the expandable device shown in FIG. 1a disposed with the vertebrae.
Figure 4:
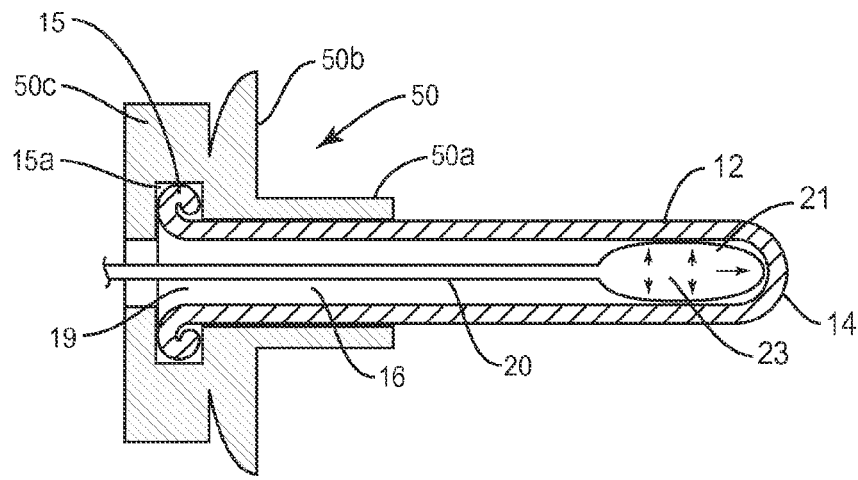
FIG. 4 is a side, cross-sectional view of an expandable device in accordance with the principles of the present disclosure.
Figure 4A:
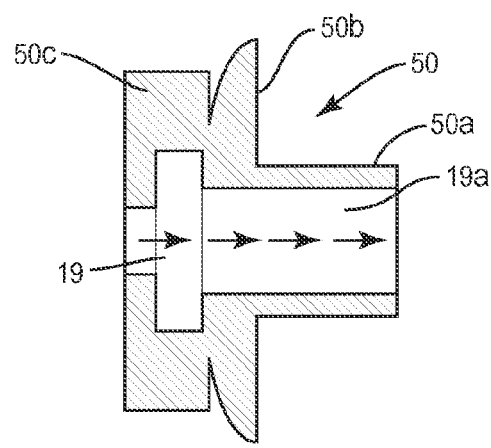
FIG. 4a is a side, cross-sectional view of a component of the expandable device shown in FIG. 4.
Figure 5:
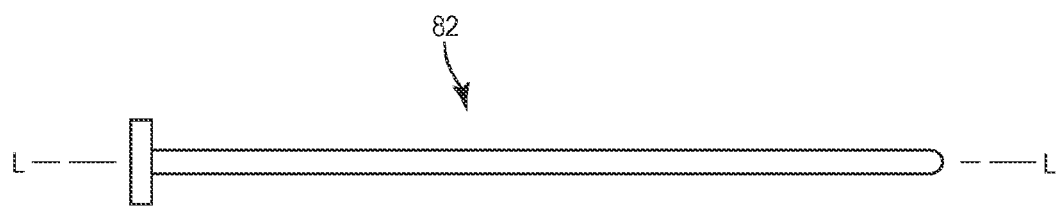
FIG. 5 is a side view of a stylet in accordance with the principles of the present disclosure.

Sleeve 12 is inserted in an access port in a lower vertebral body 40b, for example, between two endplates of the same vertebrae, as shown in FIG. 3. In an alternative embodiment, sleeve 12 is inserted adjacent a surgical site, such as, for example, between an upper vertebral body 40a and lower vertebral body 40b. In one embodiment, sleeve 12 is held in position relative to body 40a and/or body 40b with a cannula 50 configured for disposal of sleeve 12. Body 40b has a nucleus 42a that is surrounded by an annulus 44. End 14 is disposed with sleeve 12 which is positioned in nucleus 42a. Cannula 50 provides a protected access port to a disc space between bodies 40a and 40b.

Body 40a includes an inferior endplate 41a and body 40b includes a superior endplate 41b. Wall 24 and sleeve 12 expand outwardly when wall 24 moves from the deflated configuration to the inflated configuration thus causing the distance between endplate 41a and inferior endplate 41b to increase.

Cannula 50 includes an open ended access support portion 50a at a distal end of cannula 50, a handle portion 50b, and a holder portion 50c. Portion 50c defines a bore 15a configured for disposal of sleeve 12. In one embodiment, portion 50c includes a structural member in place of bore 15a that is configured to maintain the position of sleeve 20 relative to cannula 50. Portions 50a, 50b, 50c are aligned along a longitudinal axis L1 and are interconnected by an open channel 19a, which defines a lumen. Portion 50a is configured to provide guidance and support for sleeve 12 during a surgical procedure. That is, cannula 50 maintains the position and trajectory of sleeve 12 relative to a surgical site, such as, for example, a vertebral body to prevent sleeve 12 from moving relative to the surgical site during the surgical procedure.

Portion 50b is connected to portion 50c. In one embodiment, portion 50b and portion 50c are integrally formed. Portion 50b and portion 50c are configured and dimensioned to be larger than or equal to a size of sleeve 12 such that portion 50b and portion 50c secure sleeve 12 in position relative to cannula 50 during the surgical procedure. That is, portions 50b, 50c are configured to be larger than an outermost diameter of sleeve 12 when body 20 is in an inflated configuration. End 15 is folded within bore 15a to provide slack to sleeve 12 so that the amount of stretching required by sleeve 12 when body 20 moves from a deflated configuration to an inflated configuration is kept to a minimum. Body 20 is positioned inside a cavity 16 of sleeve 12 when a fillable cavity 23 of body 20 is in a deflated configuration. The amount of folding of end 15 is at a maximum when cavity 23 is in the deflated configuration. Cavity 23 is movable from a deflated configuration to an inflated configuration. When cavity 23 is in the inflated configuration, the amount of folding of end 15 decreases.

Portion 50c and portion 50b extend outwardly beyond an outer surface of sleeve 12. In one embodiment, portion 50b includes wings and portion 50c is in the shape of a bar. In one embodiment, portions 50b, 50c include semicircles. Portion 50c is configured to secure sleeve 12 in place as body 20 is inserted into sleeve 12 and cavity 23 moves from a deflated configuration to an inflated configuration.

Opening 19 in a proximal end of portion 50c is in communication with end 21. In one embodiment, opening 19 includes a valve that can be opened and closed to permit and prevent entry of a material, respectively. Opening 19 is in communication with a channel 19*a* extending through sleeve 12 such that tools and instruments may interlock or otherwise be threaded therethrough. It is envisioned that opening 19 may include various clips, protrusions detents, etc. to mate with and secure the various tools or instruments (e.g., a trocar). Channel 19*a* is configured for disposal of sleeve 12 with body 20 positioned therein. In one embodiment, end 14 extends beyond portion 50*a* when sleeve 12 engages cannula 50.

The disclosed system includes a blunt stylet 82 configured to facilitate insertion of an inflatable body, such as, for example, body 20 into a sleeve, such as, for example, sleeve 12. In one embodiment, stylet 82 has a length that extends at least from end 15 to end 14 such that stylet 82 can be used to insert body 20 within cavity 16. It is envisioned that other structures or tools may be used in place of or in addition to stylet 82 to position body 20 within cavity 16. Stylet 82 can also be used to place sleeve 12 inside vertebrate body.

In one embodiment, a trocar or sharp-ended stylet is inserted into cannula 50 when cannula 50 is positioned adjacent a surgical site, such as, for example, adjacent body 40*a* and/or body 40*b* for piercing tissue. The stylet is then removed from the surgical site and a drill used to prepare a hole into the desired location. Portion 50*b* engages portion 50*a* with sleeve 12 positioned in bore 15*a* in a folded configuration. A sleeve-port 30 is used to position sleeve 12 into a hole formed in body 40*a* or 40*b*. Sleeve-port 30 is detached from sleeve 12 and removed once sleeve 12 is positioned adjacent the surgical site, according to the preference of a medical practitioner. In one embodiment, end 15 is secured in portion 50*b* with slack so that when body 20 is inflated, sleeve 12 is not required to stretch in a significant manner.

Figure 6:
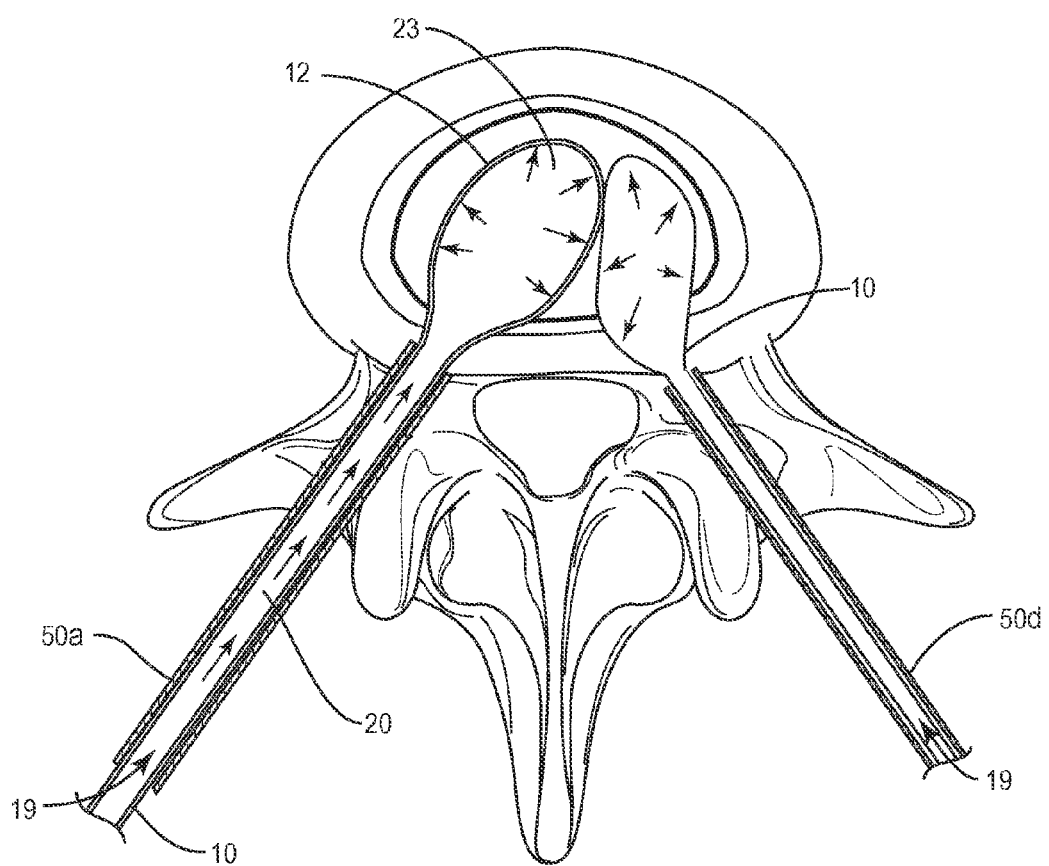
FIG. 6 is a plan view, in cross-section, of a surgical system in accordance with the principles of the present disclosure disposed with vertebrae.
Figure 7:
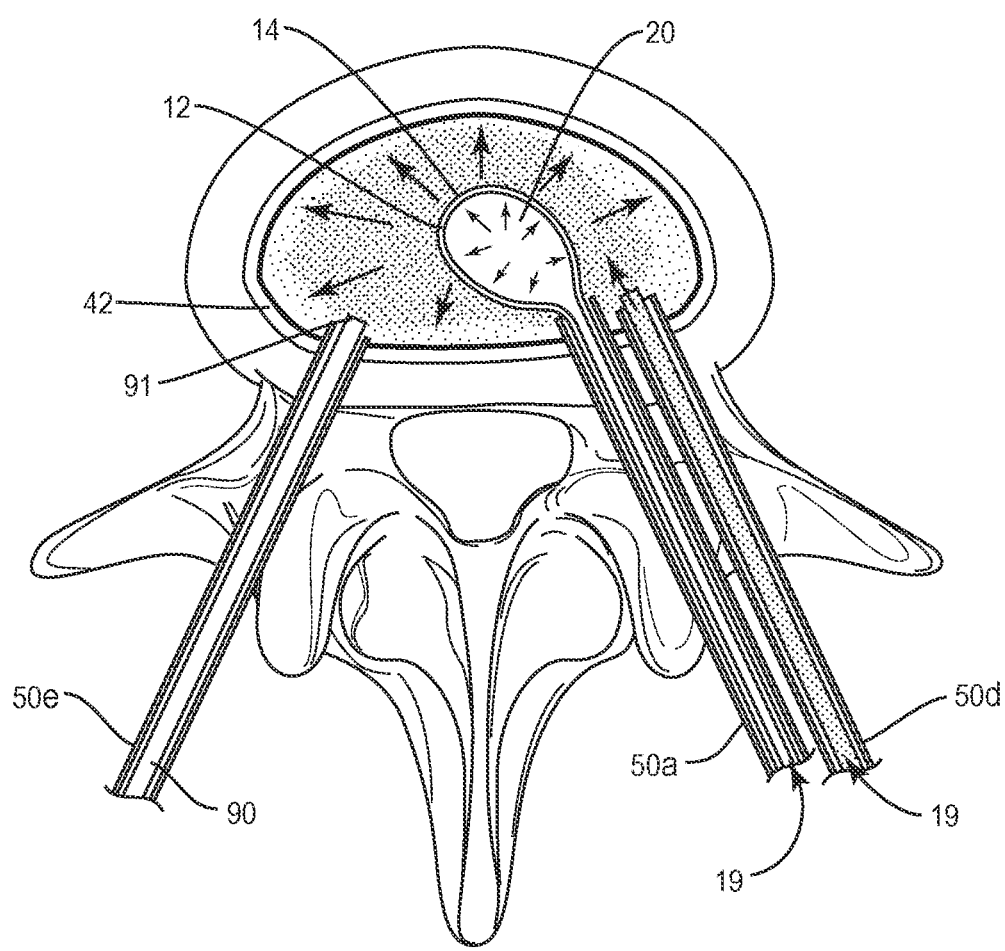
FIG. 7 is a plan view, in cross-section, of a surgical system in accordance with the principles of the present disclosure disposed with vertebrae.
Figure 8:
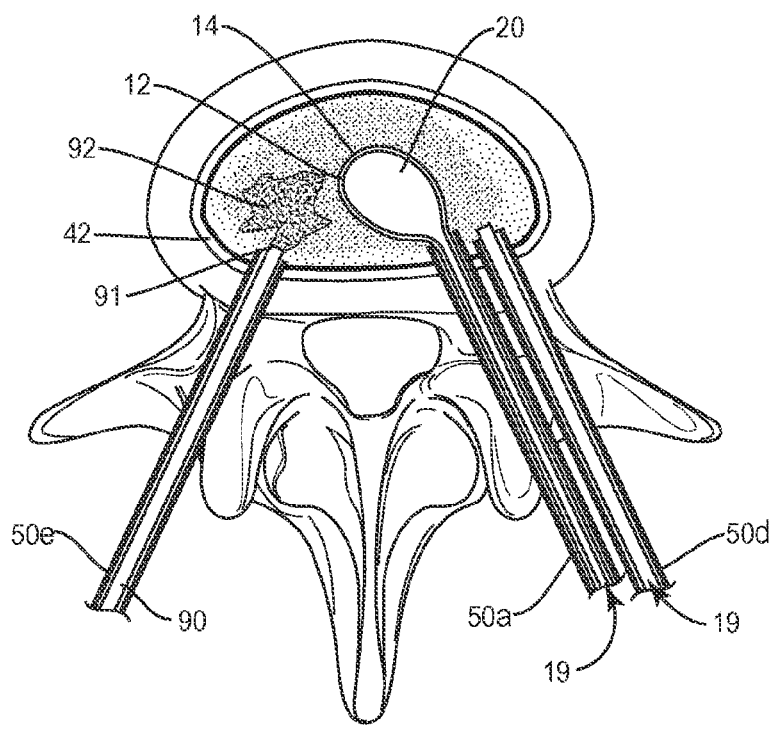
FIG. 8 is a plan view, in cross-section, of the system shown in FIG. 7 disposed with vertebrae.
Figure 9:
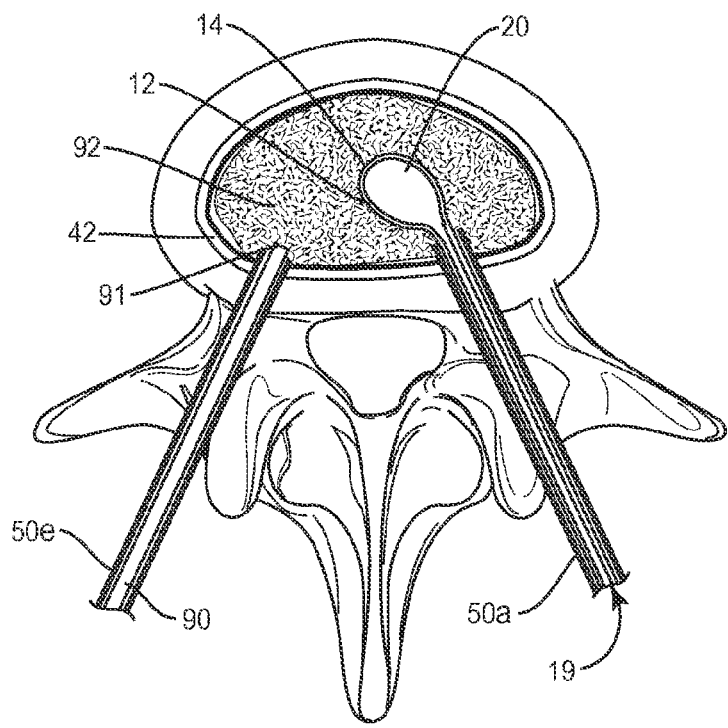
FIG. 9 is a plan view, in cross-section, of the system shown in FIG. 7 disposed with vertebrae.
Figure 10:
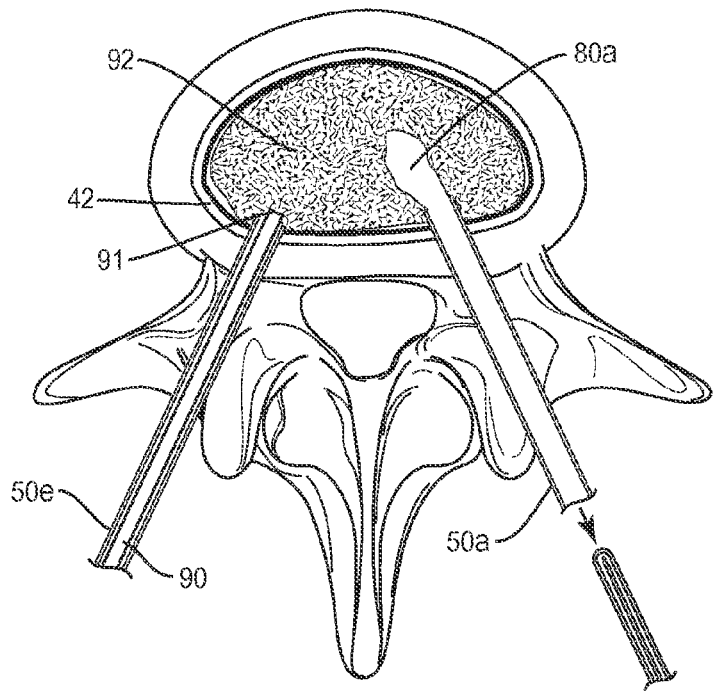
FIG. 10 is a plan view, in cross-section, of the system shown in FIG. 7 disposed with vertebrae.

In one embodiment, shown in FIG. 6, the disclosed system includes a first and second expandable device 10. Either the first or second or both expandable device can have a protective sleeve 12. Once the first and second devices are positioned in the vertebral body and expanded, the expanded portions can be positioned apart from one another or configured to touch one another. That is, cavity 23 of the second expandable device is configured to clear cancellous bone debris from a fractured bone and push the debris to a cortical wall region to create a void that can be filled with bone void filler. The void can be expanded with expansion of the first device which, will also be filled with bone void filler. The first expandable device is separately or independently inflatable from the second expandable device.

It is envisioned that the bone void filler may include, for example, materials such as stainless steel alloys, aluminum, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. The bone void filler may have material composites, including the above materials, to achieve various desired characteristics such as strength, rigidity, elasticity, compliance, biomechanical performance, durability and radiolucency or imaging preference.

The first expandable device is inserted into the tissue 49 through an access port, such as, for example, portion 50*a* of the cannula 50. Opening 19 of the first expandable device provides access to a fill tube such that cavity 23 is in communication with the fill tube and cavity 23 may expand in an outward direction that may be disposed in sleeve 12. End 14 of the first expandable device is placed adjacent to cavity 23 of the second expandable device or void 80. The second expandable device is inserted into tissue 49 through portion 50*d* of cannula 50. In one embodiment, the first and second expandable devices are inserted through the same cannula which can be configured with two separate channels, one for each of the expandable devices. Opening 19 of the second expandable device is configured to connect a fill tube with the inflatable body 20 through a channel that is in communication with the distal end of cavity 23. In one embodiment, fluid is utilized to inflate cavity 23. It is envisioned that the fluid can be a saline, contrast solution or compressed air. Once the fluid reaches cavity 23 of the second inflatable device, cavity 23 expands in an outwardly direction to create void 80 in tissue 49. In one embodiment, stylet 82 is used to insert body 20 of the second expandable device into portion 50*d* of cannula 50, stylet 82 being removed prior to inflating body 20.

Referring to FIGS. 7-11, a sleeve 12 is used to prevent rupture of a body 20 as bone cement 92 (shown in FIGS. 8-11) is injected into disc space 42 in a balloon kyphoplasty procedure. In this configuration, only one sleeve 12 is used to protect against balloon rupture, for example, to prevent rupture of the balloon when inflated as it comes in contact with cement material. In one embodiment, both IBTs can have sleeves. Cement 92 is injected through a delivery tube 90 held by an access port 50*e*. The disclosed system includes a first expandable device, such as, for example, device 10 and a second expandable device, such as, for example, device 10 positioned within sleeve 12. The first expandable device is inserted through a channel 50 and inflated by fluid directed through opening 19 of the first expandable device that is attached to a fill tube and fill source. Once filled and inflated, a body 20 of the first expandable device pushes debris from vertebral body 42 toward a cortical wall of the vertebral body. While body 20 of the first expandable device is still inflated, sleeve 12 is inserted into the vertebral body through a channel portion 50*a* to position end 14 of sleeve 12 into vertebral body 42 using either stylet 82 or sleeve-port 30 or device 10. Stylet 82 (or sleeve-port 30) is removed and the second expandable device is inserted into sleeve 12 using stylet 82, which is removed thereafter. The second expandable device is positioned such that body 20 is in close proximity to end 14 of sleeve 12. The second expandable device is filled with fluid entering opening 19, opening 19 being attached to a fill tube and fill source. The inflated body 20 of the second inflatable body is positioned in close proximity to the inflated body 20 of the first expandable device. In one embodiment, the first and the second expandable devices are inflated.

Body 20 of the first expandable device is deflated leaving void 80 in disc space 42. If a dual channel cannula is utilized, then the channel dedicated to the first expandable device is plugged following the removal of the first expandable device with a plug member to prevent leakage of bone cement 92. Bone cement 92 is delivered through delivery tube 90 attached to a bone cement source with a distal end of tube 90 extending into void 80.

Figure 11:
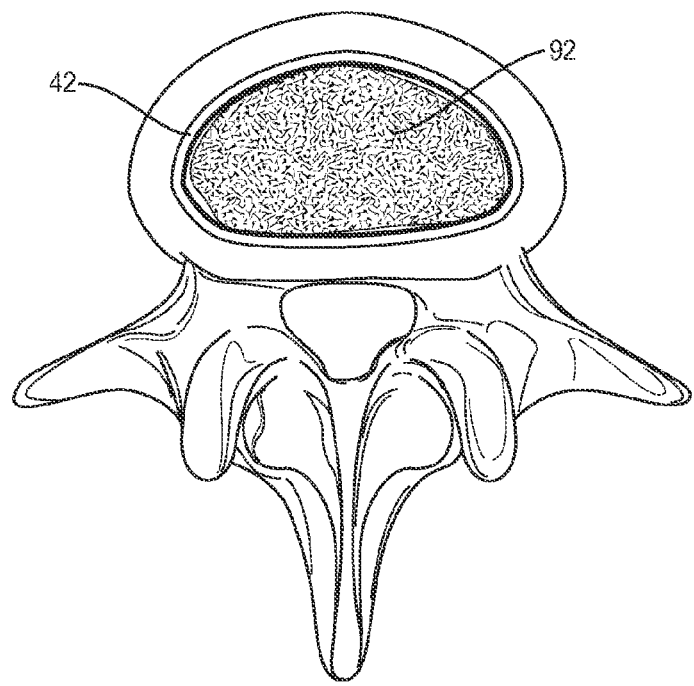
FIG. 11 is a plan view of a component of the system shown in FIG. 7 disposed with vertebrae.

The second expandable device remains inflated while bone cement 92 is delivered to void 80. The second expandable device, including sleeve 12 is then removed only after bone cement 92 has cured or at least partially cured. Bone cement 92 is then delivered to void 80*a*. To reach void 80*a*, tube 90 is moved to cannula 50*a* and inserted to void 80*a* to complete filling vertebral body 42. FIG. 11 shows cured bone cement in vertebral body 42 after the disclosed system is removed from the vertebral body.

It is envisioned that the disclosed, including first and second expandable devices 10, may be used in any existing surgical method or technique including open surgery, mini-open surgery, minimally invasive surgery and percutaneous surgical implantation.

It is contemplated that other agents and materials may be delivered to a surgical site using the disclosed system, including first and second expandable devices 10, in place of or in addition to a bone void filler. These agents include therapeutic polynucleotides or polypeptides. These agents may also include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as hydroxyapatite (HA), calcium phosphate and calcium sulfate, biologically active agents, for example, gradual release compositions such as by blending in a bioresorbable polymer that releases the biologically active agent or agents in an appropriate time dependent fashion as the polymer degrades within the patient. Suitable biologically active agents include, for example, Bone Morphogenetic Proteins (BMP), Growth Differentiation Factors (GDF) and cytokines.

In performing a method of treatment using the expandable device, it can be desirable that the compliant sleeve not adhere to tissue or other surfaces such as the bone void filler while it is curing. Thus, various coatings can be applied to wall 17, Teflon spray or silicon oil. Other coatings are also contemplated, so long as they prevent adhesion of wall 17 with bone void filler. In one embodiment, a portion of one or both of the first and second expandable devices are coated with a radioopaque or fluorescent material that is detectable by medical imaging devices so as to determine orientation and degree of inflation when placed in the bone.

It is envisioned that the use of microsurgical and image guided technologies may be employed to access, view and repair bone deterioration or damage, in conjunction with the expandable devices.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An expandable device system comprising:
   an expandable device comprising:
   an inflatable body, and
   a compliant sleeve having a longitudinal axis, the compliant sleeve including a distal end, a proximal end, and a cavity extending from the proximal end to the oppositely disposed distal end along the longitudinal axis, the cavity defined by an inner wall and an outer wall of the compliant sleeve, the distal end of the compliant sleeve forming a closed portion of the cavity and the proximal end including an opening, the cavity being configured to receive a portion of the inflatable body; and
   a cannula including a holder portion configured to secure the proximal end of the compliant sleeve to the cannula, wherein at least a portion of the compliant sleeve is folded in the holder portion following inflation of the inflatable body.

2. An expandable device system according to claim 1, wherein the holder portion is a bore extending transverse to the longitudinal axis and the inflatable body includes a fillable cavity.

3. An expandable device system as recited in claim 1, wherein the bore is defined in part by opposite first and second inner surfaces of the cannula that extend transverse to the longitudinal axis and opposite third and fourth inner surfaces of the cannula that extend parallel to the longitudinal axis, the third and fourth inner surfaces each extending between the first and second inner surfaces.

4. An expandable device system as recited in claim 1, wherein the cannula includes a central passageway that is coaxial with the longitudinal axis, the expandable device extending through the central passageway, the cannula being free of any passageways that surround the central passageway and extend parallel to the longitudinal axis.

5. An expandable device system as recited in claim 1, further comprising:
   a sleeve-port configured to enter the cavity through the opening to insert the complaint sleeve into or adjacent a surgical site, the sleeve-port comprising a tapered distal end and a handle at a proximal end of the sleeve-port, the handle having a maximum diameter perpendicular to the longitudinal axis that is greater than that of the cavity; and
   a blunt stylet configured to facilitate insertion of the inflatable body into the cavity, the blunt stylet having a maximum length along the longitudinal axis that is equal to or greater than a maximum length of the compliant sleeve along the longitudinal axis.

6. An expandable device system comprising:
   a first expandable device having:
   an inflatable body, and
   a compliant sleeve along a longitudinal axis, the compliant sleeve having a cavity extending from a proximal end to an oppositely disposed distal end along the longitudinal axis, the cavity defined by an inner wall and an outer wall of the compliant sleeve, the distal end forming a closed portion of the cavity and the proximal end including an opening, the cavity being configured to receive a portion of the inflatable body;
   a cannula including a holder portion configured to secure the proximal end of the compliant sleeve to the cannula, wherein at least a portion of the compliant sleeve is folded in the holder portion following inflation of the inflatable body; and
   a second expandable device including an inflatable body, wherein the inflatable body of the first expandable device is configured to form a void of a first size and the inflatable body of the second expandable device is configured to form a void of a second size, wherein the void of the second size is larger than the void of the first size.

7. An expandable device system according to claim 6, wherein the holder portion is a bore extending transverse to the longitudinal axis and the inflatable body includes a fillable cavity.

8. An expandable device system according to claim 6, further comprising a material delivery device configured to deliver bone void filler to the first void and the second void.

9. An expandable device system according to claim 8, wherein the bone void filler comprises polymethylmethacrylate (PMMA).

10. An expandable device system according to claim 6, wherein the compliant sleeve comprises silicon.

11. An expandable device system according to claim 6, wherein a thickness between the inner and outer wall is within a range of 0.001 inches to 0.010 inches.

12. An expandable device system according to claim 6, wherein the cannula further comprises a handle portion, the cannula holder portion and the cannula handle portion being configured to be larger than an outermost diameter of the compliant sleeve in a fully extended position.

13. An expandable device system according to claim 6, wherein the cannula further comprises an open access support portion configured to provide guidance and support for the compliant sleeve.

14. An expandable device system according to claim 6, wherein the compliant sleeve is configured to have slack when the inflatable body of the first expandable device is in a deflated configuration.

15. A method for performing spinal surgery comprising:
providing the expandable device system of claim 6;
accessing a vertebral body;
inserting said first expandable device into the vertebral body;
inflating said inflatable body of said first expandable device to create a first void in the vertebral body;
inserting said second expandable device into the vertebral body;
inflating the inflatable body of said second expandable device to create a second void in the vertebral body;
deflating the inflatable body of said first expandable device and removing said first expandable device from the vertebral body after inflating the inflatable body of said second expandable device;
inserting bone void filler into at least a portion of the first void and allowing said inserted bone void filler to at least partially cure;
deflating the inflatable body of said second expandable device and removing the inflatable body of said second expandable device and the compliant sleeve from the vertebral body after insertion, the bone void filler into the first void; and
filling the second void with bone void filler.

16. An expandable device system as recited in claim 6, wherein the cannula extends along the longitudinal axis between a first end having a first end surface and an opposite second end having a second end surface, the first end comprising the holder portion, the end surfaces extending perpendicular to the longitudinal axis, the cannula comprising a passageway having a first opening extending through the first end surface and a second opening extending through the second end surface, the first opening having a maximum diameter that is less than that of the second opening.

17. An expandable device system as recited in claim 6, wherein the at least a portion of the compliant sleeve is folded in the holder portion prior to inflation of the inflatable body, an amount of folding of the at least one portion of the complaint sleeve being at a minimum prior to inflation of the inflatable body.

18. An expandable device system as recited in claim 6, further comprising a valve positioned within the opening, the valve being configured to open and close to permit and prevent entry of material into the cavity.

19. An expandable device system as recited in claim 6, wherein the holder member defines a first channel in the cannula configured for disposal of the first expandable device and the cannula includes a second channel that is separate from the first channel and configured for disposal of the second expandable device.

20. An expandable device system comprising:
an expandable device comprising:
an inflatable body, and
a compliant sleeve defining a longitudinal axis, the compliant sleeve including a cavity extending from the proximal end of the compliant sleeve to an oppositely disposed distal end of the complaint sleeve along the longitudinal axis, the distal end of the compliant sleeve forming a closed portion of the cavity and the proximal end including an opening, the cavity being configured to receive a portion of the inflatable body;
a cannula including a holder portion configured to secure the proximal end of the compliant sleeve to the cannula;
a sleeve-port configured to enter the cavity through the opening to insert the complaint sleeve into or adjacent a surgical site, the sleeve-port comprising a handle having a maximum diameter that is greater than that of the cavity; and
a blunt stylet configured to facilitate insertion of the inflatable body into the cavity, the blunt stylet having a maximum length along the longitudinal axis that is equal to or greater than a maximum length of the compliant sleeve along the longitudinal axis.

* * * * *